United States Patent [19]  [11] 3,931,340
Nishihara et al.  [45] Jan. 6, 1976

[54] CHLORINATION OF AROMATIC COMPOUNDS

[75] Inventors: Akio Nishihara; Hidekastu Kato; Yaoki Jimbo; Yoshiro Tomoda; Jinichi Omi, all of Tokyo, Japan

[73] Assignee: Asahi Denka Kogyo K.K., Tokyo, Japan

[22] Filed: May 23, 1974

[21] Appl. No.: 472,657

Related U.S. Application Data

[62] Division of Ser. No. 378,217, July 11, 1973, Pat. No. 3,916,014.

[30] Foreign Application Priority Data

Aug. 3, 1972  Japan................................ 47-77975
Aug. 3, 1972  Japan................................ 47-77976

[52] U.S. Cl.......... 260/623 H; 260/619 R; 260/619; 260/620; 260/625
[51] Int. Cl.²........................................ C07C 39/28
[58] Field of Search........ 260/623 H, 619 A, 619 B, 260/620, 625, 619 R, 649

[56] References Cited
UNITED STATES PATENTS 2,410,497  11/1946  Hentrich et al................. 260/623 H
3,510,529  5/1970   Van Ee........................... 260/623 H
3,542,882  11/1970  Ashall............................ 260/623 R

FOREIGN PATENTS OR APPLICATIONS 1,157,540  7/1969  United Kingdom............. 260/623 H

OTHER PUBLICATIONS

Kosuwa et al., "J. Organic Chem." Vol. 28: pp. 630–633.
Clarens "Chem. Abstracts" Vol. 16, p. 2440 (1972).
Cini et al., "Chem. Abstract" Vol. 56, p. 14971c.

*Primary Examiner*—James O. Thomas, Jr.
*Assistant Examiner*—W. B. Lone
*Attorney, Agent, or Firm*—Woodhams, Blanchard and Flynn

[57] ABSTRACT

Nuclear chlorination of aromatic compounds having an electron donating group is effected by contacting said aromatic compound with copper (II) chloride in an aqeuous hydrochloric acid solution and adding chlorine to the reaction system to maintain the mole ratio of (a) copper (I) chloride to (b) the sum of copper (I) chloride plus copper (II) chloride at more than 0.005/1 but less than about 0.3/1.

4 Claims, No Drawings

CHLORINATION OF AROMATIC COMPOUNDS

This is a division of application Ser. No. 378,217, filed July 11, 1973, now U.S. Pat. No. 3,916,014.

BACKGROUND OF THE INVENTION

1. Field of the Invention

This invention relates to nuclear chlorination of aromatic compounds having an electron donating group, particularly phenols and aromatic amines.

2. Description of the Prior Art

The nuclear chlorination of aromatic compounds having an electron donating group is known. For example, the chlorination of phenols by cupric chloride in hot aqueous hydrochloric acid is disclosed in Japanese Pat. publication No. Sho 45-40882 (40882/70), dated Dec. 22, 1970. The process disclosed in this publication is advantageous in comparison with prior processes because the ratio of the desired para-substituted product to the ortho-substituted product is increased and less severe reaction conditions are required.

Additional descriptions of this process and related processes are set forth in (1) H. P. Crocker and R. Walser, J. Chem. Soc. (c), 1970, 1982–1986, (2) H. P. Crocker and R. Walser, Chem. and Ind., 1969, 1141–1142, and (c) German Offen. Nos. 1800676, 1926852 and 2014773.

In the process of the above-referenced Japanese patent publication, for economic reasons, after the chlorination reaction is completed, the solution of copper chlorides dissolved in aqueous hydrochloric acid solution (hereinafter referred to as the "working solution") is separated from the organic products. The working solution is then oxidized with a molecular oxygen-containing gas and hydrogen chloride gas to convert the cuprous chloride therein to cupric chloride and the working solution is then recycled for use in the next chlorination reaction. This is a batchwise recycling method. It is also proposed to carry out a continuous method in which the chlorination of the aromatic compound and the oxidation of cuprous chloride to cupric chloride are carried simultaneously by introducing hydrogen chloride gas and molecular oxygen-containing gas into the chlorination reaction solution.

There are some disadvantages in the above-mentioned processes. In the case of the above-mentioned batchwise recycling method, the concentration of cupric chloride in the chlorination reaction solution is reduced as the chlorination reaction progresses and the rate of the chlorination reaction falls remarkably. To keep the conversion of phenols at about 80–90%, it is necessary to chlorinate for a long time or to use a large excess of cupric chloride, such as 3–5 times the theoretical amount. It is evident that such a method has numerous disadvantages, including increased cost of equipment because of the additional reaction vessel required for regenerating the working solution, increased cost of catalyst, reduction of the manufacturing capacity because of the additional regeneration process, and the cost of expensive reaction and regeneration materials.

In the case of the continuous method, some advantages are achieved such as lowering of the catalyst cost, shortening of the reaction time because of a higher reaction rate and obtaining a good conversion with less cupric chloride than is the case with the recycle method. But the continuous method does not avoid other disadvantages such as increased cost of equipment and the use of expensive materials, and the need for expensive safety precautions because of the use of oxygen gas and hydrogen chloride gas. In this continuous system, if the concentration of hydrogen chloride is reduced, there is an increase of unwanted by-products and a reduction of the yield of the desired product, so that the introduction of hydrogen chloride gas is indispensable. Also, air cannot be used, in practice, as an oxygen source because much hydrogen chloride accompanies the unreacted gas (waste gas), and the concentration of hydrogen chloride in the chlorination reaction liquid decreases. The equipment and cost of recovering hydrogen chloride from the unreacted gas are substantial items of expense. It is necessary, therefore, to use oxygen gas for practical industrial operation of the process in order to reduce the volume of the unreacted gas.

In this prior art, the reaction of aniline is illustrated by the following reaction equations.

$(C_6H_5NH_2.HCl)_2.CuCl_2 +$
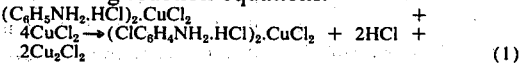
$4CuCl_2 \rightarrow (ClC_6H_4NH_2.HCl)_2.CuCl_2 + 2HCl +$
$2Cu_2Cl_2$ (1)
$2Cu_2Cl_2 + 4HCl + O_2 \rightarrow 4CuCl_2 + 2H_2O$ (2)

Therefore, it is required to use 1 mole of hydrogen chloride gas per one mole of aniline. An additional quantity of hydrogen chloride gas is needed to maintain the required concentration of hydrogen chloride in the water which is formed in the reaction. Furthermore, the chlorinated aniline is separated from the reaction system as the complex of cupric chloride and chlorinated aniline hydrochloride. Therefore, it is necessary to use more than 2 moles of hydrogen chloride gas per 1 mole of aniline.

Furthermore, in the prior art, the overall reaction rate is not sufficiently fast. The oxidation step of cuprous chloride to cupric chloride is the overall rate determining step, because of the very small solubility of oxygen gas in the reaction solution.

SUMMARY OF THE INVENTION

We have discovered an economical chlorination process capable of reducing the above-mentioned disadvantages. Our process has high selectivity for the para-chloro-substitution product, and gives a high yield. In our process the chlorination of the aromatic compound and the oxidation of cuprous chloride to cupric chloride are effected at the same time by introducing chlorine gas into the reaction solution containing cupric chloride, hydrogen chloride and the aromatic compound. It is not required to use other oxidizing agents, such as oxygen gas.

It is an object of this invention economically to produce chlorinated aromatic compounds which have electron donating group, such as chlorinated aromatic amines and chlorinated phenols, with higher selectivity to para-chloro-substitution products and a faster reaction rate.

The process of the present invention for preparing a chlorinated aromatic compound consists essentially of reacting (1) an aromatic compound having an electron donating group, preferably an aromatic compound selected from the group consisting of aromatic amines and phenols, (2) aqueous hydrochloric acid (hydrogen chloride) and (3) cupric chloride, with the addition of (4) chlorine gas to the reaction mixture.

Preferably the rate of addition of chlorine gas is controlled to keep the mole ratio of (a) cuprous chloride to (b) the sum of cuprous chloride and cupric chloride, at more than 0.005, more preferably at 0.02 to 0.15.

The aromatic amines used as starting materials for preparing the desired chlorinated aromatic amine final products in the present invention have the formula (I):

$$ArNR^1R^2 \qquad (I)$$

wherein $R^1$ and $R^2$ represent members selected from the group consisting of hydrogen, alkyl having 1 to 12 carbon atoms and aralkyl group having 7 to 12 carbon atoms, and $R^1$ and $R^2$ can be the same or different; Ar represents a member selected from the group consisting of phenyl and naphthyl, which can be unsubstituted or substituted by hydroxy, alkoxy having 1 to 6 carbon atoms, halogen, or $-NR^1R^2$ group (wherein $R^1$ and $R^2$ are as defined above), provided that Ar has at least one substitutable hydrogen at the 2, 4 or 6 positions relative to the $-NR^1R^2$ group.

Preferred aromatic amines of the formula (I) are aniline, N-methyl aniline, N,N-dimethyl aniline, o-, m- or p-anisidine, o-, m- or p-phenetidine, o-, m or p-chloro aniline, o-phenylene diamine, α- or β-naphthylamine, o-, m- or p-toluidine, o-, m- or p-xylidine, p-ethyl aniline, o-tertiary butyl aniline and 2,6-di-tertiary butyl aniline. Especially preferred aromatic amines of the formula (I) are the aromatic amines whose hydrochlorides are separable as a precipitate from reaction mixture, for example, o-toluidine, because the reaction product can be separated easily, and the filtrate can be used for the next chlorinating reaction with addition of more o-toluidine starting material.

The phenols used as starting materials for preparing the desired chlorinated phenol final products in present invention have the formula (II):

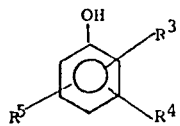

wherein $R^3$ represents a member selected from the group consisting of (a) hydrogen, (b) hydroxy, (c) halogen, (d) alkyl group having 1 to 4 carbon atoms which is either unsubstituted or substituted on the 1 to 5 positions of the alkyl group by aryl, hydroxy aryl, mono-halogenated hydroxy aryl, hydroxyl, carboxyl or their functional derivatives, and (e) aryl which is either unsubstituted or substituted by halogen, and/or alkyl group having 1 to 3 carbon atoms; $R^4$ and $R^5$, which can be the same or different, represent a member selected from the group consisting of (a) hydrogen, (b) alkyl having 1 to 4 carbon atoms which is either unsubstituted or substituted on the 1 to 5 positions of the alkyl group by aryl, hydroxy aryl, mono-halogenated hydroxyl aryl, hydroxyl, carboxyl, or their functional derivatives, but when $R^5$ is hydrogen, $R^3$ and $R^4$ can both be halogen atoms; and the phenol of formula (II) has at least one substitutable hydrogen atom on the 2, 4 or 6 positions relative to the hydroxyl group of the phenol.

Preferred phenols of the formula (II) are phenol, o- or p-phenyl phenol, o-chloro phenol, m-cresol, thymol, resorcinol, m-xylenol, p-chloro phenol and o-cresol.

The chlorination reaction temperature can vary depending on the particular aromatic compound used as starting material, but generally a temperature of 70° to 150°C, preferably 80° to 110°C, is employed for aromatic amines, and a temperature of 85° to 130°C is employed for phenols.

It is preferred to use a high concentration of hydrogen chloride in the reaction mixture. In general the HCl concentration is 5 to 12 N, preferably 7 to 10 N, for aromatic amines, and generally the concentration is more than 2 N, preferably more than 3 N, for phenols.

The mole ratio of cupric chloride plus cuprous chloride to aromatic starting material is not critical, but this ratio preferably is in the range of 0.5 to 5:1 because the reaction is very slow and it is difficult to control the chlorine gas feed rate when this ratio is too small.

Metal chlorides, in addition to cupric chloride, for example, LiCl, NaCl, $MgCl_2$, $CaCl_2$, $CdCl_2$, $AlCl_3$ and $FeCl_3$, can be present in the reaction mixture of the present invention, and some of them have an effect as an accelerator of the reaction.

The reaction can be carried out at atmospheric pressure or at a pressure of 1 to 2 kg/cm² (gauge pressure).

Cupric chloride employed in the process of the present invention is made present in the reaction system by adding thereto anhydrous cupric chloride, cupric chloride dihydrate, or a material which is converted to cupric chloride in hot aqueous hydrochloric acid, for example, cupric oxide, cupric sulfate, or cupric acetate or a material which is converted to cupric chloride by chlorine in the reaction solution, for example, cuprous oxide, cuprous chloride, or cuprous acetate.

The mole ratio of (a) cuprous chloride to (b) the sum of cuprous chloride and cupric chloride preferably is more than 0.005/1 and, more preferably is more than 0.02/1. The latter ratio of more than 0.02/1 is employed to inhibit formation of tar and to permit substantial tolerance in the amount of chlorine introduced. But when a large amount of copper chlorides are present in reaction solution, that is, when the ratio of (b) the sum of cupric chloride and cuprous chloride to (c) the aromatic compounds is very large, the mole ratio of (a) cuprous chloride to (b) the sum of cuprous chloride and cupric chloride can be kept at about 0.005/1.

Furthermore, the mole ratio of (a) cuprous chloride to (b) the sum of cuprous chloride and cupric chloride can be maintained as high as 0.2 to 0.3, but the reaction rate is reduced in this range. Therefore, it is preferred to maintain the mole ratio of (a)/(b) at about $$\frac{0.02 \text{ to } 0.15}{1.0}$$

While a constant reaction rate can be obtained by maintaining constant the mole ratio of (a) cuprous chloride to (b) the sum of cuprous chloride and cupric chloride, the present invention comprehends introducing chlorine intermittently, and allowing said mole ratio of (a)/(b) to vary within the stated limits.

Generally, in the chlorination of aromatic compounds having electron donating group in aqueous hydrochloric acid, the ratio of para-chloro substituted product to ortho-chloro substituted product is 1–2/1. The chlorination process cannot avoid the formation of considerable amounts of tar and high-boiling materials (dichloro substituted or trichloro substituted materials).

But, surprisingly, under the specially controlled conditions of the present invention, the ratio of para-chloro substituted product to ortho product is very high as is shown in the following examples, and very small amounts of higher chlorinated products and tar are obtained.

The specially controlled conditions leading to this advantageous result are obtained by introducing a suitable amount of chlorine gas into the reaction mixture to maintain the mole ratio of (a) cuprous chloride to (b) the sum of cuprous chloride plus cupric chloride at more than 0.005/1.0, more preferably at more than 0.02/1.0.

Under such condition, the chlorine taken in the reaction solution is immediately preferentially consumed for effecting an oxidation reaction of cuprous chloride to cupric chloride, and the chlorination of the aromatic compound is effected essentially by the cupric chloride and the chlorine gas does not substantially react directly with the aromatic starting material. Therefore the ratio of para-chloro substituted product is very high, and the formation of higher chlorinated products and tar is minimized.

In case there is supplied an excess amount of chlorine gas, i.e., more than that required to maintain the mole ratio of (a)/(b) in the above-stated range, the selectivity to the para product is reduced, and the formation of tar increases.

The method of introducing chlorine gas into reaction solution can be selected suitably from known methods, for example, bubbling pure or highly concentrated chlorine gas into the reaction solution by means of a gas introducing pipe or gas sparger.

Preferred methods of introducing chlorine gas into reaction solution are as follows; the first method is to introduce chlorine gas into the gas phase of the reaction vessel so that the chlorine gas is taken into the reaction solution from the surface of the reaction solution; the second method is to introduce chlorine gas into the gas phase of the reaction vessel and the reaction solution is continuously recycled and gushed into the gas phase and chlorine gas is thereby taken into the reaction solution; the third method is to mix the chlorine gas outside the reaction vessel with the gases removed from the gas phase of the reaction vessel (preferably, this gas is an inert gas such as nitrogen gas) and then bubbling this gas mixture into the reaction solution with a gas introducing pipe.

The amount of chlorine gas introduced into the reaction solution is controlled easily as follows: in the case of the first method, by controlling the speed of stirring of the reaction solution, the chlorine partial pressure and the configuration of the baffle; in case of the second method, by controlling the chlorine partial pressure, the amount of recycled liquid and the style of the gushing method; in case of the third method, by controlling the chlorine partial pressure, the amount of recycled gas, the speed of stirring and the type of bubbling method employed for bubbling the gas into the reaction solution.

The method of introducing chlorine to the reaction solution is not critical, and for example, besides the above-mentioned preferred methods, chlorine can be introduced into the reaction solution as an aqueous chlorine solution or liquefied chlorine can be bubbled into the solution.

The method of the present invention is distinguished from the prior art methods because no additional oxidizing agent, such as oxygen gas, needs to be added as is done in the above-mentioned batchwise reaction and continuous reaction. However, the effectiveness of the reaction is not harmed by the presence of a minor amount of oxygen gas in the reaction system.

The reaction of the present invention is shown by the combination of the following reaction equations in case of 2-methyl aniline.

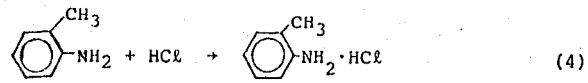  (4)

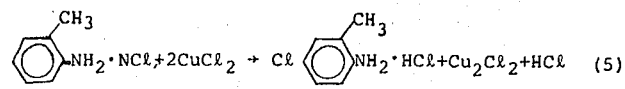  (5)

$$Cl_2 + H_2O \rightarrow HClO + HCl \tag{6}$$

$$HClO + HCl + Cu_2Cl_2 \rightarrow 2CuCl_2 + H_2O \tag{7}$$

Therefore, the net reaction is indicated as the following equations as sum of the equations (4), (5), (6) and (7),

  (8)

and cupric chloride may be considered to be a chemical catalyst.

The basic mode of the industrial practice of the present invention, in the case of the starting material 2-methyl aniline as a preferred example, is as follows:

4-chloro-2-methyl aniline hydrochloride which is produced as an end product by the process of the present invention, precipitates in the reaction solution, and is filtered off at hot temperature. It is then washed with aqueous hydrochloric acid to remove the copper chlorides. The filtrate mixed with the washings is mixed with fresh 2-methyl aniline to form a reaction solution. Then chlorine is introduced to the reaction solution, and the chlorination reaction is carried out. Or alternatively, hydrochloric acid and a part of the water can be distilled from the mixture of the filtrate and the washings, and then to this distillate 2-methyl aniline is added, and then this mixture is mixed with the reaction solution (i.e., the residue of the distilled mixture of the washings and the filtrate), and chlorination is then carried out. In either case, theoretically, hydrochloric acid gas need not be supplied to the reaction solution, although in practice make-up hydrochloric acid will normally be required.

Although the conversion of starting aromatic material to the chlorinated end product can be kept at a low level, so that the withdrawn unreacted aromatic starting material can be recycled as a part of the raw starting material of the next reaction, normally the conversion of the starting material is easily maintained at a high level such as 80 to 90%. It is not preferred to achieve conversions of 98 to 99%, because of the possibilities of forming higher chlorinated materials and tar. The process of the invention can be carried as a batchwise process, a semi-continuous process or a continuous process.

The present invention provides an improved process for the chlorination of aromatic compounds, which process has economical and industrial advantages and achieves higher selectivity of the desired para-substituted product.

In particular, the present invention provides an improved process of chlorinating aromatic compound, which process has many advantages compared with the above-mentioned prior art processes in which chlorination of the aromatic compound and oxidation of the cuprous chloride with oxygen and hydrochloric acid gas are carried out separately. The reaction time is shortened because of the very high reaction rate, the total manufacturing time is shortened, the reaction process is simpler, a high reaction rate is achieved more rapidly, the catalyst cost is lower or a larger production capacity is obtained because the amount of cupric chloride employed can be reduced to less than the theoretical amount (2 mole per 1 mole of aromatic compound), and there is higher selectivity to the desired para-substituted product.

Similarly, the present invention provides an improved process of chlorination having many advantages compared with the above-mentioned prior art process comprising chlorination of aromatic compound and oxidation of cuprous chloride with oxygen and hydrochloric acid gas simultaneously, such as the use of lower price raw material (i.e., chlorine gas) as compared with anhydrous hydrochloric acid gas and oxygen, easier control of the by-products because the concentration of hydrochloric acid increases as the reaction progresses, and the shortening of the reaction time because of the very high reaction rate.

The invention is further described in the following illustrative examples, which are not limiting.

EXAMPLE 1

Into a 500 ml flask, equipped with a thermometer, a stirrer and a gas inlet tube, were added 200 ml of 7 N-hydrochloric acid solution, 0.28 moles of copper (II) chloride dihydrate, 0.03 moles of copper (I) chloride and 0.2 moles of 2-methylaniline hydrochloride. After replacing the air in the vapor space of the flask with nitrogen gas, the stirred mixture was heated to 90°C, then the flask was closed and chlorine gas was introduced into the closed vapor space of the flask at a rate of 0.0146 moles/hr for 13 hours, while the speed of the stirrer was kept at 180–200 r.p.m.

During the reaction, samples of the reaction mixture were withdrawn periodically and the amount of copper (I) chloride based on the sum of copper (I) chloride and copper (II) chloride was measured iodometrically. The results are shown in the following table.

| Reaction time (hrs.) | 3 | 6 | 9 | 13 |
|---|---|---|---|---|
| Amount of copper (I) chloride (mole %) | 9.5 | 8.9 | 8.3 | 8.0 |

The resulting mixture was cooled to 40°C and 0.25 moles of sodium sulfite was added with mixing. Then the mixture was neutralized with an excess of ammonia solution. The oil liberated was collected and the aqueous layer was extracted with chloroform. The extract together with the collected oil, were dehydrated and on distillation under reduced pressure gave an oil (27.5 g) and tar (0.05 g). The composition of this oil is shown below (by gas chromatography):

| 2-methylaniline | 3.79% |
|---|---|
| 6-chloro-2-methylaniline | 0.06% |
| 4-chloro-2-methylaniline | 95.05% |
| 4,6-dichloro-2-methylaniline | 0.10% |

EXAMPLE 2

The apparatus described in Example 1 was used. A mixture of N,N-dimethyl aniline (0.2 moles) and 223 g of 22.9 wt. % hydrochloric acid solution was poured into the flask, and to this solution, 0.28 moles of copper (II) chloride dihydrate and 0.03 moles of copper (I) chloride were added. The reaction was carried out at 90°C with stirring, while introducing chlorine gas into the closed vapor space of the flask at 0.018 moles/hr for 10 hours. The amount of copper (I) chloride was controlled to be between 2.7 mole % and 4.1 mole % throughout the reaction. The reaction mixture was treated in the same fashion as in Example 1, and 28.2 g of the distilled oil was obtained. This oil had the following composition (by gas chromatography).

| N,N-dimethyl aniline | 8.92% |
|---|---|
| 6-chloro-N,N-dimethyl aniline | 0.01% |
| 4-chloro-N,N-dimethyl aniline | 90.79% |
| 4,6-dichloro-N,N-dimethyl aniline | 0.28% |

EXAMPLE 3

Into a flask as described in Example 1, 223 g of 22.9 wt. % hydrochloric acid solution, 0.36 moles of copper (II) chloride, 0.04 moles of copper (I) chloride and 0.2 moles of aniline hydrochloride were introduced. With stirring, the reaction was carried out at 98°–100°C for 15 hours, while chlorine gas was introduced into the vapor space of the flask at 0.0126 moles/hr.

The amount of copper (I) chloride was controlled between 5.9 mole % and 8.3 mole % throughout the reaction. The reaction mixture was treated in the same fashion as Example 1, and 25.1 g of distilled oil was collected. This oil had the following composition by gas chromatography.

| Aniline | 3.71% |
|---|---|
| 2-chloro aniline | 0.05% |
| 4-chloro aniline | 95.84% |
| 2,4-dichloro aniline | 0.04% |

EXAMPLE 4

A mixture of 223 g of 22.9 wt. % hydrochloric acid solution, 0.28 moles of copper (II) chloride dihydrate, 0.03 moles of copper (I) chloride and 0.2 moles of p-anisidine were placed in a flask as described in Example 1. With stirring at 180–200 r.p.m., the reaction was carried out at 90°–95°C, for 9 hours, while chlorine gas was introduced into the closed vapor space of the flask at 0.02 moles/hr.

The amount of copper (I) chloride was controlled between 9.7 and 8.6 mole % throughout the reaction. By following the procedure of Example 1, the distilled products were found to contain p-anisidine (9.07%), 2-chloro-p-anisidine (90.97%) and trace amount of dichloro-p-anisidine. The yield of 2-chloro-p-anisidine was 98.2% based on the reacted p-anisidine.

EXAMPLE 5

Into a flask as described in Example 1, 223 g of 22.9 wt. % hydrochloric acid solution, 0.28 moles of copper (II) chloride dihydrate, 0.02 moles of copper (I) chloride and 0.2 moles of α-naphthylamine hydrochloride were introduced. With stirring at 180–200 r.p.m., the reaction was carried out at 95°C for 6 hours, while chlorine gas was introduced into the closed vapor space of the flask at 0.06 moles/hr.

The amount of copper (I) chloride was maintained between 6.7 and 5.1 mole %.

The stirred mixture was cooled and the solid was filtered off. The solid was suspended in water, then stirred with sodium sulfite and an excess of ammonia solution. The liberated base was collected and distilled under reduced pressure.

The distilled oil (36 g) had the following composition by gas chromatography.

| | |
|---|---|
| α-naphthylamine | 9.7% |
| 2,4-dichloro-α-naphthylamine | 86.0% |
| 4-chloro-α-naphthylamine | 4.3% |

EXAMPLE 6

Into a 2 liter flask, equipped with a thermometer, a stirrer, a gas-inlet tube and reflux condenser, 1000 ml of 7 N-hydrochloric acid solution, 1.8 moles of copper (II) chloride dihydrate, 0.2 moles of copper (I) chloride and 1 mole of 2-methylaniline hydrochloride were introduced. After replacing the air in the vapor space of the flask with nitrogen gas, at 90°C, the gases in the space of the flask were started to recycle from the condenser to the reaction mixture through the gas-inlet tube, by using a gas circulating pump. The reaction was carried out at 90°C for 8 hours with stirring at 180–200 r.p.m., while the volume of the circulating gas was kept at 15 l/hr. and chlorine gas was introduced into the delivery tube of the pump at 0.12 moles/hr. The amount of copper (I) chloride was between 9.0 and 5.2 mole % throughout the reaction.

The solid 4-chloro-2-methylaniline hydrochloride was filtered off while the mixture was still hot, and washed with a small amount of 7 N-hydrochloric acid solution.

The solid was suspended in 350 g of water, and to this stirred suspension sodium sulfite was added. After confirming that there were no copper (II) ions in this suspension, the resulting mixture were neutralized with an excess of gaseous ammonia.

The liberated oil was extracted with chloroform, dried and distilled under reduced pressure. A crude 4-chloro-2-methylaniline oil (120.5 g) and tar (0.5 g) were obtained. This oil had the following composition by gas chromatography.

| | |
|---|---|
| 2-methylaniline | 2.5% |
| 6-chloro-2-methylaniline | 0.04% |
| 4-chloro-2-methylaniline | 97.20% |
| 4,6-dichloro-2-methylaniline | 0.26% |

Further, into the filtrate and washings, were added 0.9 moles of 2-methylaniline hydrochloride and an amount of copper (II) chloride dihydrate which corresponded to the amount of copper lost in the filtration process. By using this solution, the second reaction (repeated reaction) was carried out for 8 hours under the same conditions as described above. The amount of copper (I) chloride was between 7.5 and 5.2 mole %.

By following the same procedure of this example, distilled oil (130.1 g) and tar (0.47 g) were obtained. The composition of the oil is as follows.

| | |
|---|---|
| 2-methylaniline | 1.77% |
| 6-chloro-2-methylaniline | 0.03% |
| 4-chloro-2-methylaniline | 98.10% |
| 4,6-dichloro-2-methylaniline | 0.10% |

EXAMPLE 7

Into a 2 liter flask equipped with a thermometer, a stirrer, a gas introducing tube and a reflux condenser, 1000 ml of 7 N-hydrochloric acid solution, 1.8 moles of copper (II) chloride dihydrate, 0.2 moles of copper (I) chloride and one mole of 2-methylaniline hydrochloride were added. With stirring at 180–200 r.p.m., the reaction was carried out at 90°C for 9 hours, while chlorine gas was passed into the reaction mixture at the rate of 0.1 moles/hr.

The waste gas from the condenser was washed with dilute caustic soda solution. The amount of copper (I) chloride was between 6.3 and 4.7 mole % throughout the reaction. By following the same procedure as Example 4, 4-chloro-2-methylaniline hydrochloride was separated, neutralized, extracted dried and distilled under reduced pressure, a crude distilled oil (118.7 g) and tar (1.4 g) were obtained.

The composition of this oil is as follows.

| | |
|---|---|
| 2-methylaniline | 3.6% |
| 6-chloro-2-methylaniline | 0.03% |
| 4-chloro-2-methylaniline | 96.08% |
| 4,6-dichloro-2-methylaniline | 0.29% |

EXAMPLE 8

Into a 500 ml flask equipped with a thermometer, a stirrer and a gas-inlet tube, 200 ml of 6.5 N-hydrochloric acid solution, 0.28 moles of copper (II) chloride, 0.03 moles of copper (I) chloride and 0.2 moles of phenol were added. After replacing the air in the vapor space of the flask with nitrogen gas, the reaction was carried out at 95°C for 13 hours with stirring at 180–200 r.p.m., while chlorine gas was introduced into the closed vapor space of the flask at 0.014 moles/hr.

During the reaction, samples of the reaction mixture were withdrawn periodically and the amount of copper (I) chloride based on the sum of copper (I) chloride and copper (II) chloride was measured iodometrically. The results are shown in the following table.

| Reaction time (hrs) | 3 | 6 | 9 | 13 |
|---|---|---|---|---|
| Amount of copper (I) chloride (mole %) | 9.2 | 8.5 | 7.9 | 7.5 |

The resulting mixture was cooled and organic materials were extracted with benzene. The extract was dried and distilled under reduced pressure. Distilled oil (24 g) was obtained and this had the following composition by gas chromatography.

| phenol | 7.2% |
|---|---|
| o-chlorophenol | 7.6% |
| p-chlorophenol | 81.1% |
| 2,4-dichlorophenol | 4.1% |

EXAMPLE 9

Into a flask as described in Example 8, 200 ml of 6.5 N-hydrochloric acid solution, 0.28 moles of copper (II) chloride, 0.03 moles of copper (I) chloride and 0.2 moles of m-xylenol were added. With stirring, the reaction was carried out at 95°C for 13 hours, while chlorine gas was introduced into the closed vapor space of the flask at 0.014 moles/hr. The ratio of copper (I) chloride was controlled between 8.6 and 7.2 mole % throughout the reaction. By following the same procedure as Example 8, distilled oil (28.2 g) was obtained and it had the following composition by gas chromatography.

| m-xylenol | 3.7% |
|---|---|
| o-chloro-m-xylenol | 6.5% |
| p-chloro-m-xylenol | 88.5% |
| 2,4-dichloro-m-xylenol | 1.3% |

EXAMPLE 10

The apparatus as described in Example 8 was used. Into the flask, 200 ml of 6N-hydrochloric acid solution, 0.29 moles of copper (II) chloride dihydrate, 0.02 moles of copper (I) chloride and 0.2 moles of o-chlorophenol were added. With stirring, the reaction was carried out at 95°–98°C for 11 hours, while chlorine gas was introduced into the closed vapor space of the flask at 0.014 moles/hr.

The amount of copper (I) chloride was controlled between 6.3 and 4.6 mole % throughout the reaction.

By following the same procedure as described in Example 8, the distilled oil was found to contain o-chlorophenol (25.2%), 2,4-dichlorophenol (70.8%), 2,6dichlorophenol (3.1%) and 2,4,6-trichlorophenol (0.9%).

The yield of 2,4-dichlorophenol was 94.7% based on the reacted o-chlorophenol.

EXAMPLE 11

Into a flask as described in Example 8, 200 ml of 6 N-hydrochloric acid solution, 0.5 moles of copper (II) chloride dihydrate, 0.02 moles of copper (I) chloride and 0.2 moles of o-cresol were added. With stirring at 180°–200 r.p.m., the reaction was carried out at 95°–98°C for 9 hours, while chlorine gas was introduced into the closed vapor space of the flask at 0.02 moles/hr. The amount of copper (I) chloride was controlled between 3.9 and 2.3 mole %. By following the procedure of Example 8, the distilled oil was found to contain o-cresol (8.8%), p-chloro-o-cresol (87.4%), o-chloro-o-cresol (3.8%) and trace of dichloro-o-cresol by gas chromatography.

The yield of p-chloro-o-cresol was 94.9% based on the reacted o-cresol.

The embodiments of the invention in which an exclusive property or privilege is claimed are defined as follows:

1. A process for the nuclear mono chlorination of a phenol of the formula

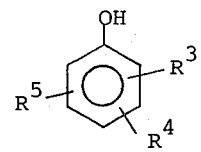

wherein $R^3$ is hydrogen; hydroxy; halogen; alkyl having one to 4 carbon atoms; alkyl having 1 to 4 carbon atoms substituted by aryl, hydroxy aryl, monohalogenated hydroxy aryl, hydroxyl, or carboxyl; aryl; or aryl substituted by halogen, alkyl having 1 to 3 carbon atoms or halogen and said latter alkyl; $R^4$ and $R^5$, which are the same or different, are hydrogen; alkyl having 1 to 4 carbon atoms; alkyl having one to 4 carbon atoms substituted by aryl, hydroxy aryl, monohalogenated hydroxy aryl, hydroxyl or carboxyl; provided that when $R^5$ is hydrogen, $R^3$ and $R^4$ can both be halogen, provided further that said phenol has at least one replaceable hydrogen on the 2, 4 or 6 positions relative to the phenolic hydroxyl, which comprises: contacting in the liquid phase, reactants consisting essentially of
   A. said phenol
   B. from 0.5 to 5.0 moles of copper (I) chloride plus copper (II) chloride, per mole of said phenol, and
   C. an aqueous solution of hydrochloric acid providing a concentration of hydrochloric acid in the reaction system of more than 2N,
at a temperature in the range of 85° to 130°C, at a pressure in the range of from atmospheric to about 2 kg/cm² gauge, and adding to the reaction system chlorine gas to convert copper (I) chloride to copper (II) chloride, the chlorine gas being supplied at a rate effective to maintain the mole ratio of (a) copper (I) chloride/(b) copper (I) chloride plus copper (II) chloride, in the range of from 0.005/1 to 0.15/1, throughout the reaction to obtain a reaction product comprised predominantly of said phenol monochlorinated by replacement of one of said replaceable hydrogens by chlorine.

2. A process according to claim 1, in which the phenol is selected from the group consisting of phenol, m-xylenol, o-chloro phenol and o-cresol.

3. A process according to claim 1, in which the rate of addition of chlorine to the reaction system is controlled to maintain the mole ratio of (a) copper (I) chloride/(b) copper (I) chloride plus copper (II) chloride in the range of from 0.02/1.0 to 0.15/1.0 during the reaction.

4. A process according to claim 1, in which the phenol is selected from the group consisting of phenol, o-phenyl phenol, p-phenyl phenol, o-chloro phenol, m-cresol, thymol, resorcinol, m-xylenol, p-chloro phenol and o-cresol.

* * * * *